(12) United States Patent
Dufour

(10) Patent No.: US 9,933,400 B1
(45) Date of Patent: Apr. 3, 2018

(54) APPARATUS FOR IMAGING THROUGH A VISCOUS SUBSTANCE

(71) Applicant: INSTITUT NATIONAL D'OPTIQUE, Québec (CA)

(72) Inventor: Denis Dufour, Québec (CA)

(73) Assignee: INSTITUT NATIONAL D'OPTIQUE, Quebec, Quebec (CA)

( * ) Notice: Subject to any disclaimer, the term of this patent is extended or adjusted under 35 U.S.C. 154(b) by 0 days.

(21) Appl. No.: 15/473,049

(22) Filed: Mar. 29, 2017

(51) Int. Cl.
*G01F 23/00* (2006.01)
*G01N 33/00* (2006.01)
*G01N 22/00* (2006.01)

(52) U.S. Cl.
CPC ............. *G01N 33/00* (2013.01); *G01N 22/00* (2013.01)

(58) Field of Classification Search
CPC ....... H04N 1/0318; H04N 2201/02495; G02B 3/0075
See application file for complete search history.

(56) References Cited

U.S. PATENT DOCUMENTS

| 5,331,178 A | * | 7/1994 | Fukuda | ................... B21B 27/10 250/239 |
| 2008/0188839 A1 | * | 8/2008 | Chan | ................... A61B 18/203 606/9 |

* cited by examiner

*Primary Examiner* — Kiho Kim
(74) *Attorney, Agent, or Firm* — Merchant & Gould P.C.

(57) ABSTRACT

An optical system is for imaging a surface covered with a viscous substance using an illuminating beam having a spectral profile including an imaging waveband to which the viscous substance is transparent. The system includes a support frame, a flattening plate, a light source and a camera. The support frame has a front and a rear end, and has an abutment structure. The flattening plate is transparent to the imaging waveband, and is engageable with the viscous substance to flatten the substance into a substantially flat layer. The light source is operatively coupled to the support frame, and configured to project the illuminating beam towards the surface through the flattening plate. The camera is mounted onto the support frame, is sensitive to light in the imaging waveband, and has a field of view encompassing at least a portion of the surface illuminated by the illuminating beam.

17 Claims, 3 Drawing Sheets

APPARATUS FOR IMAGING THROUGH A VISCOUS SUBSTANCE

TECHNICAL FIELD

The technical field generally relates to optical imaging, and more particularly concerns an optical system for imaging a surface covered with a viscous substance and a method for doing the same.

BACKGROUND

In the petroleum industry, visual inspection of containers in which are stored petroleum products, residues, and derivatives is considered important to assess their physical integrity, and prevent possible ruptures due to defects (e.g. cracks and/or corrosion) present on the surface of the containers.

More generally, the presence of opaque and viscous residues on a surface of such containers makes visual inspection of the surface difficult, and impossible in some circumstances. For at least this reason, the opaque and viscous residues often need to be removed to allow visual inspection of the surfaces of the containers. However, removal of such residues is a laborious and costly task that may even generate hazardous and toxic substances.

There is thus a need for an apparatus for inspecting surfaces covered by opaque and viscous substances that addresses at least some of the challenges presented above.

SUMMARY

In accordance with one aspect, there is provided an optical system for raging a surface covered with a viscous substance using an illuminating beam having a spectral profile including an imaging waveband to which the viscous substance is transparent. The optical system includes a support frame, a flattening plate, a light source and a camera, The support frame has a front end and a rear end, and includes an abutment structure defining a surface-abutting plane at the front end. The flattening plate is transparent to the imaging waveband, and extends across the support frame rearwardly of the surface-abutting plane. The flattening plate is engageable with the viscous substance to flatten the same into a substantially flat layer. The light source is operable to generate the illuminating beam and is operatively coupled to the support frame so as to project the illuminating beam towards the surface through the flattening plate. The camera is sensitive to light in the imaging waveband and is mounted onto the support frame. The camera has a field of view encompassing at least a portion of the surface illuminated by the illuminating beam.

In one embodiment, the system includes a biasing assembly configured to bias the flattening plate towards the surface-abutting plane.

In one embodiment, the biasing assembly includes a flange and least one spring. The flange projects inwardly of the support frame rearwardly of the flattening plate. The at least one spring is mounted between the flange and the flattening plate.

In one embodiment, the flattening plate has two surfaces coated with an anti-reflection coating.

In one embodiment, the abutment structure includes a plurality of legs each having a forward extremity configured to engage the surface through the viscous substance.

In embodiment, each leg further includes a surface-engaging wheel mounted at the forward extremity.

In one embodiment, the system includes an articulated arm. The articulated arm has a distal extremity configured to be affixed to an anchoring point and a proximal extremity. The proximal extremity includes a frame-mounting structure configured for connection with the support frame.

In one embodiment, the light source and the camera are mounted proximate the rear end of the support frame.

In one embodiment, the imaging waveband includes a terahertz waveband extending from 0.15 to 0.6 terahertz.

In one embodiment, the flattening plate is made of a polyethylene thermoplastic material.

In one embodiment, the light source includes at least one gigahertz sub-source and a frequency multiplier.

In one embodiment, the camera is a terahertz-sensitive camera.

In one embodiment, the system includes a processor for processing images of the surface.

In one embodiment, the system includes a display for displaying the processed images of the surface.

In one embodiment, the field of view of the camera is at most 30×20 cm.

In accordance with another aspect, there is provided an optical method for imaging a surface through a viscous substance using an illuminating beam having a spectral profile including an imaging waveband to which the viscous substance is transparent. The optical method includes the steps of: flattening the viscous substance into a substantially flat layer with a flattening plate transparent to the imaging waveband; projecting the illuminating beam towards the surface through the flattening plate; detecting return light from at least a portion of the surface illuminated by the illuminating beam; and processing the return light to obtain an image of said surface.

In one embodiment, the method further includes a step of displaying the image of the surface.

In one embodiment, the step of detecting return light from at least a portion of the surface illuminated by the illuminating beam includes a sub-step of receiving specular reflection from the at least a portion of the surface illuminated by the illuminating beam.

Other features and advantages of the present description will become more apparent upon reading of the following non-restrictive description of specific embodiments thereof, given by way of example only with reference to the accompanying drawings.

DETAILED DESCRIPTION

Figure 1:
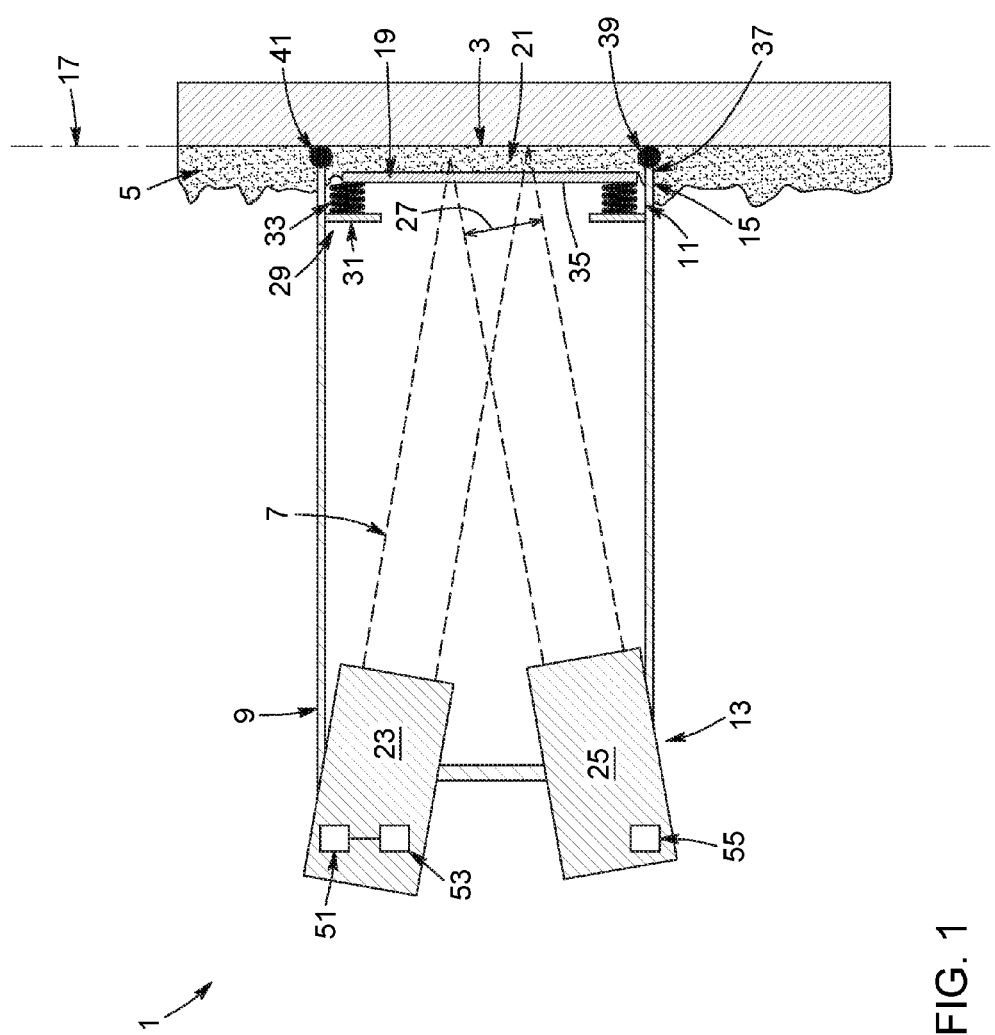
FIG. 1 is a schematized representation of an optical system for imaging a surface covered with a viscous substance according to one embodiment.

In the following description, similar features in the drawings have been given similar reference numerals, and, to not unduly encumber the figures, some elements may not be indicated on some figures if they were already identified in one or more preceding figures. It should also be understood herein that the elements of the drawings are not necessarily depicted to scale, since emphasis is placed upon clearly illustrating the elements and structures of the present embodiments.

The present description generally relates to an optical system for imaging a surface through a viscous substance.

In the present description, the expression "optical imaging system "optical system", "imaging system", "system", derivatives and variants thereof refers to an apparatus configured to acquire images representative of a surface to be inspected. The optical system could further be understood as a device configured to sense and/or probe light reflected by the surface to be inspected, according to the needs of a particular application. Advantageously, in embodiments of the present description the optical system may provide clear and undistorted images of the surface despite the presence of a viscous substance that covers it.

The expression "viscous substance" may be understood as referring to a substance substantially resistant to gradual deformation by shear or tensile stress. In the present description, the term encompasses, but is not limited to, substances comprising hydrocarbon product(s), oily residue(s), or the like. An example of a viscous substance are petroleum residues. More generally, the term "viscous substance" may refer to any material (liquid or solid) that sticks on a surface.

The expression "surface covered with a viscous substance" may refer to various scenarios in which the viscous substance is provided (i.e. is present) on the surface to be inspected. For example, the expression encompasses the scenario in which the viscous substance extends over a portion (i.e. a limited area) of the surface. The expression also encompasses the scenario in which the viscous substance extends over the whole surface. The surface may also be continuously covered (i.e. the viscous substance forms a continuous layer on the surface) or discontinuously covered (i.e. the viscous substance forms a discontinuous layer on the surface and may comprise, for example, pinholes, uncovered area, or the like) with the viscous substance. It will be readily understood that the expression is not limited by the area covered by the viscous substance or the orientation of the surface (i.e. the spatial orientation of the surface).

Some embodiments of the present invention may be particularly useful in the field of active imaging. The embodiments described below are designed for carrying out tasks of material surface inspection, and more particularly non-destructive inspection, testing or evaluation, when, for example, the solid surface to be inspected is covered with a viscous substance having an uneven surface. Because of its uneven surface, the viscous substance scrambles more or less substantially the electromagnetic radiation reflected by the surface to image, which typically results in severe image distortions. In some implementations, the optical system may be used in the petroleum industry, e.g. for inspecting surfaces of containers containing petroleum products, derivatives and the like. Alternatively, the optical system may be used in the food, agri-food, packaging industries, or in any other industry wherein active imaging of a surface covered with substance may be useful.

Referring to FIG. 1, an embodiment of an optical system 1 for imaging a surface 3 through a viscous substance 5 is shown.

Generally described, the optical system 1 uses an illuminating beam 7. The illuminating beam 7 has a spectral profile, which includes an imaging waveband to which the viscous substance 5 is transparent.

In the present description, the terms "light" and "optical", "spectral profile" and "waveband", derivatives and variants thereof, are used to refer to radiation in any appropriate region of the electromagnetic spectrum and, more particularly, are not limited to visible light. By way of example, the imaging waveband may cover or substantially correspond to the terahertz waveband, which may be of particular interest for applications in the petroleum industry, as petroleum products are typically transparent to at least some optical frequencies lying in this range. For example, the imaging waveband may encompass electromagnetic radiation having optical frequencies in a terahertz band extending from 0.15 THz to 0.6 THz. Alternatively, the imaging waveband could comprise optical frequencies extending from 0.1 THz to 4 THz, depending on the optical properties of the viscous substance 5 covering the surface 3.

It will be readily understood that the term "transparent" refers to a property of transmitting at least a portion, and in some case the entirety of a specific imaging waveband (i.e. the property of not absorbing a significant portion of the imaging waveband of the illuminating beam). It will be readily understood that in some implementations full transparency over the optical spectrum or over the imaging waveband may not be necessary to meet the working requirements of the present system, and that the level of light transmission of various components of the system may depend on the particularities of a given application.

The optical system 1 comprises a support frame 9 having a front end 11 and a rear end 13. The support frame 9 can be made of plastic, polymer, metal, alloys, combinations thereof, or of any other suitable materials having the desired structural properties. By way of example, in one variant the support frame 9 may be made of aluminum and have a length (spacing between both front and rear ends) of about 100 cm and a cross-section of about 50×50 cm$^2$. It will be understood that the support frame 9 may be embodied by a plurality of components assembled together defining a volume that admits the insertion of a plurality of elements, or a structure onto which a plurality of elements may be mounted. It will also be understood that the size and dimensions of the support frame 9 may vary according to the needs of a particular application. Optionally, the support frame 9 may be an open structure, i.e. a structure having some openings. Alternatively, the support frame 9 could include a plurality of sidewalls assembled together to form a closed casing.

The support frame 9 includes an abutment structure 15 defining a surface-abutting plane 17 at the front end 11 of the support frame 9. In the illustrated embodiment, the abutment structure 15 comprises a plurality of legs 37, and each one of the legs 37 has a forward extremity 39 configured to engage with the surface 3 through the viscous substance 5.

In one example of implementation, each leg 37 comprises a surface-engaging wheel 41 mounted at the forward extremity 39, so that the wheels can slide onto the surface 3 under inspection. Alternatively, each leg 37 could comprise a surface-engaging runner (not shown). It will be readily understood that the surface-engaging wheels 41 or runners may be useful to move or to facilitate the displacement of the optical system 1 onto the surface 3. Furthermore, the surface-engaging wheels 41 (or the surface-engaging runners) may be motorized (i.e. the optical system 1 may comprise a motor powering the surface-engaging wheels 41 and/or runners), so as to allow the optical system 1 to be automatically displaced onto the surface 3 to be inspected, hence allowing automated imaging of a large extent of the surface. It will be understood that the surface-engaging wheels 41 or runners could either be in contact with the surface 3 (i.e. the surface-engaging wheels 41 or the runners may directly touch the surface 3) or in indirect contact with the surface 3 (e.g. a thin layer of viscous substance 5 or other residue may be present between the surface-engaging wheels 41 or the runners and the surface 3).

In other variants, the abutment structure 15 could include an engaging element instead of the plurality of legs 37. In this configuration, for example, the engaging element may be a single continuous piece having an O-shaped cross-section (or a cross-section forming another closed shape) and may be mounted at the front end 11 of the support frame 9. The cross-section of the engaging element may conform to the cross-section of the support frame 9, so that the illuminating beam 7 may freely pass through a center portion of the engaging element to illuminate the surface 3 while a peripheral portion may engage with the surface 3 through the viscous substance 5. In this example; the engaging element may confine a portion of the viscous substance 5 within its perimeter so as to flatten the viscous substance 5 into a substantially flat layer 21. Alternatively, the engaging element may comprise a plurality of individual parts assembled together and forming a piece having an O-shaped cross-section.

The optical system 1 also includes a flattening plate 19. The material of the flattening plate 19 and its thickness are chosen in such a way that the plate 19 is transparent in the imaging waveband of the spectral profile of the illuminating beam 7. The flattening plate 19 can be made, for example, of polytetrafluoroethylene (PTFE, e.g. Teflon®), a polyethylene thermoplastic material (e.g. high-density-polyethylene (HDPE)), polymethylpentene (TPX), float-zone silicon, or of any other material transparent in the imaging waveband. It will be understood that the flattening plate 19 may be a element made of a single piece or embodied by a plurality of parts assembled together and having the required optical properties to allow transmission of at least a portion of the imaging waveband. Optionally, the flattening plate 19 may be provided with anti-reflection coatings 35 to limit the reflections of the illuminating beam 7 on both surfaces of the flattening plate 19. The anti-reflection coating 35 may be useful to minimize unwanted specular reflections and helps optimizing the transmission of the illuminating beam 7 through the flattening plate 19. For example, and without being limitative, the anti-reflection coating 35 can be a layer of parylene or a sheet of porous Teflon®, depending on the material forming the flattening plate 19.

In one embodiment, one side of the flattening plate 19, e.g. the one that is in contact with the viscous substance 5, may be made of Teflon® or a similar non-stick material to minimize adhesion of the viscous substance to the flattening plate 19 when the latter needs to be removed after completion of an inspection run. Optionally, the entire flattening plate 19 may be made of Teflon® or a similar non-stick material.

As illustrated, the flattening plate 19 extends across the front end 11 of the support frame 9, and rearwardly of the surface-abutting plane 17. The surface-abutting plane 17 is defined as the plane encompassing the points of contact of the abutment structure 15 with the surface 3. The flattening plate 19 is engageable with the viscous substance 5 to flatten at least a portion of the viscous substance 5 into a substantially flat layer 21. The substantially flat layer 12 is confined between the exterior side surface of the flattening plate 19, the surface 3, and the abutment structure 15 (i.e. the plurality of legs 37 or the surface engaging element).

In some implementations, the optical system 1 also includes a biasing assembly 29 configured to bias the flattening plate 19 towards the surface-abutting plane 17.

By way of example, in the illustrated variant the biasing assembly 29 includes a flange 31. The flange 31 projects inwardly of the support frame 9, and rearwardly of the flattening plate 19. The biasing assembly 29 also includes at least one spring 33 that connects the flange 31 to the flattening plate 19. Each spring 33 can be, for example, a flat spring or a coiled spring. It will be understood that the spring(s) 33 could be replaced by any other element having an elastic (deformable) body that can recover its initial shape when released after being deformed and that can press against the viscous substance 5 through the flattening plate 19. For example, and without being limitative, the spring(s) 33 could be replaced by insert(s) made up of any resilient material such as a shape-memory alloy, or the like. Alternatively, one or more pistons (not shown) could be connected to the flattening plate 19 to bias it forward of the support structure. The piston can be, for example a pneumatic piston or a hydraulic piston.

As will be readily understood by one skilled in the art, the biasing assembly 29 is preferably configured to press against the viscous substance 5 via the flattening plate 19 so as to form the substantially flat layer 21. It will be understood that the biasing assembly 29 acts as a mechanism for pressing against the viscous substance 5, and should not be limited to the variants discussed above.

Optionally, the optical system 1 may include a motor powering the biasing assembly 29. The motor can be an electric motor, a heat engine, or any type of motor, and can be used to automatically adjust and/or allow fine tuning of the pressure applied onto the viscous substance 5.

The optical system 1 also includes a light source 23. The light source 23 generates the illuminating beam 7, and is preferably mounted on the support frame 9 or otherwise operatively coupled thereto so as to project the illuminating beam 7 towards the surface 3 through the flattening plate 19.

In the illustrated embodiment, the light source 23 is mounted proximate the rear end 13 of the support frame 9. Alternatively, the light source 23 could be mounted anywhere on the support frame 9 (e.g. on a side of the support frame 9). The light source may project the illuminating beam directly towards the surface 3 or indirectly through intermediate optical components. In other variants, the light source may be physically separate from the support frame and the illuminating beam projected towards the surface via the use of suitable optical components.

In one embodiment, the light source 23 generates an illuminating beam 7 having a spectral profile including an imaging waveband centered on an optical frequency of about 0.3 THz (i.e. centered on a wavelength of about 1 mm). Such a center frequency can be obtained by using a plurality of sub-sources. For example, the light source 23 may comprise at least one gigahertz sub-source 51 and a frequency multiplier 53. The frequency multiplier 53 can be embodied, for example, by an electronic circuit that generates an output signal whose frequency is an integer multiple (i.e. a harmonic) of the frequency of the input signal. In such a configuration, the frequency multiplier 53 may generate an output signal having a center optical frequency in the THz while receiving an input signal with a center optical frequency in the GHz. For example, and without being limitative, the at least one sub-source 51 could be a SAGE Millimeter Inc. tuned Gunn Oscillator having a 96-GHz frequency output and the frequency multiplier 53 could be a frequency tripler.

The optical system 1 also includes a camera 25 sensitive to light in the imaging waveband. The camera 25 is mounted onto the support frame 9 and has a field of view 27 encompassing at least a portion of the surface 3 illuminated by the illuminating beam 7. Alternatively, the field of view 27 could encompass an entirety of the illuminated portion of the surface 3.

As illustrated, the camera 25 is mounted proximate the rear end 13 of the support frame 9. Alternatively, the camera 25 could be mounted anywhere onto the support frame 9 (e.g. on a side of the support frame 9). The camera 25 may be positioned and oriented towards the illuminated portion of the surface 3 to capture the light reflected from the surface 3, but may also capture the light from the surface 3 via the use of intermediate optical components (e.g. mirror, lenses, or the like).

In some embodiments, the camera 25 may be fixed to the support frame 9 and the spacing between the camera 25 and the surface 3 may be kept constant. The focus of the camera 25 may be pre-adjusted, and the spatial resolution of the images (i.e. mm/pixel) may be selected and set prior to use of the imaging system 1. For example, the optical system 1 may be used to image (i.e. detect) specular reflections from the surface 3.

In some embodiments, the camera 25 is a terahertz-sensitive camera and is sensitive to an imaging waveband comprising frequencies in the range from 0.1 to 4 THz.

In some embodiments, the field of view 27 of the camera 25 is adjustable.

The optical system 1 may further include additional optical elements coupled with the camera 25, so as to produce a focused and undistorted image of the surface 3.

In some embodiments, the optical elements of the objective lens of the camera or the additional optical elements may be made up of a material such as float-zone silicon or polyethylene (e.g. high-density-polyethylene) to reduce the total weight of the optical system 1.

In some embodiments, the optical system 1 may also include a data acquisition unit mounted onto the support frame 9 and connected to the camera 25, The data acquisition unit comprises a processor 55 for processing images of the surface 3 and a display 57 for displaying the images. Optionally, the optical system 1 includes means for locally storing and/or viewing images.

In some embodiments, the optical system 1 is configured to send unprocessed images to a remote electronic processing, recording and display system(s). The data acquisition unit may be remote from the optical system 1 and the optical system 1 may further include a communication link for sending the unprocessed images captured by the camera 25 to the processor 55. The processor 55 is preferably configured to process the raw images and to send the processed images of the surface 3 to a recording, storing and displaying system(s).

Figure 2:
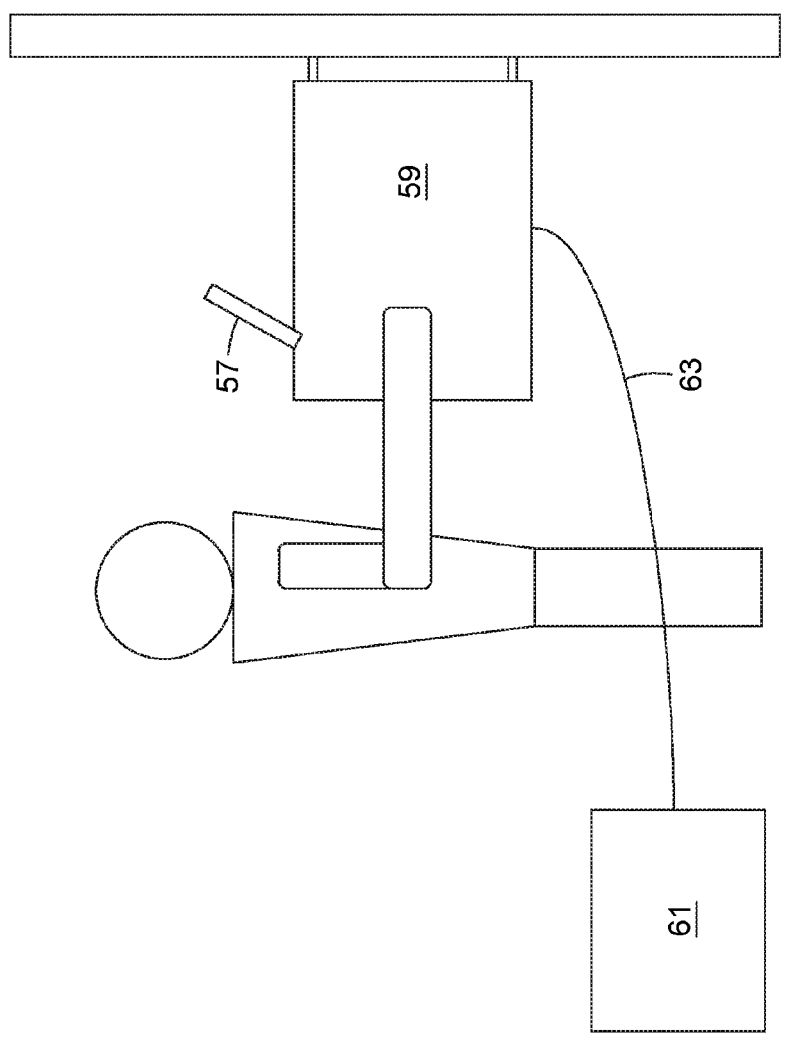
FIG. 2 illustrates an optical system for imaging a surface covered with a viscous substance according to one embodiment.

Referring now to FIG. 2, in one example of implementation the light source 23 and the camera 25 may be mounted inside the support frame 9 and be sufficiently lightweight so that the optical system 1 can be manually carried by a human operator.

In the illustrated embodiment, the optical system 1 includes an instrument head 59 in which is mounted the support frame or which may embody the support frame. The optical system 1 of this variant also includes a display 57 for displaying processed images of the surface 3. The optical system 1 further includes a power supply 61 operatively connected to the instrument head 59 with electrical cabling 63.

As illustrated, the display 57 is mounted onto the instrument head 59. Alternatively, the display 57 and the power supply 61 may be located outside of the instrument head 59 to reduce its weight. The display screen 57 could be, for example, a small digital display attached on a top portion of the instrument head 59. The small digital display allows to look at processed images of the surface 3, and may further inform the operator of the current status (i.e. provides feedback) of the optical system 1.

The light weight and size required for the instrument head 59 to be portable may be achieved by using one (or several) small GHz sub-sources 51 such as a SAGE Millimeter Inc. tuned Gunn Oscillator (96 GHz frequency output), combined with a frequency tripler to provide an illuminating beam having a wavelength of approximately 1 mm.

The optical system 1 according to this embodiment comprises components which have been previously described, such as lightweight custom-designed HDPE optical elements for the light source 23 and the camera 25, and a small lightweight camera (e.g. the INO MICROXCAM-384i-THz camera having a 384×288 pixel array). Furthermore, the optical system 1 also includes a flattening plate 19 made from lightweight Teflon® or HDPE (highly transparent to wavelengths around 1 mm). The flattening plate 19 may also comprise an anti-reflection coating 35, as it has been previously described.

Figure 3:
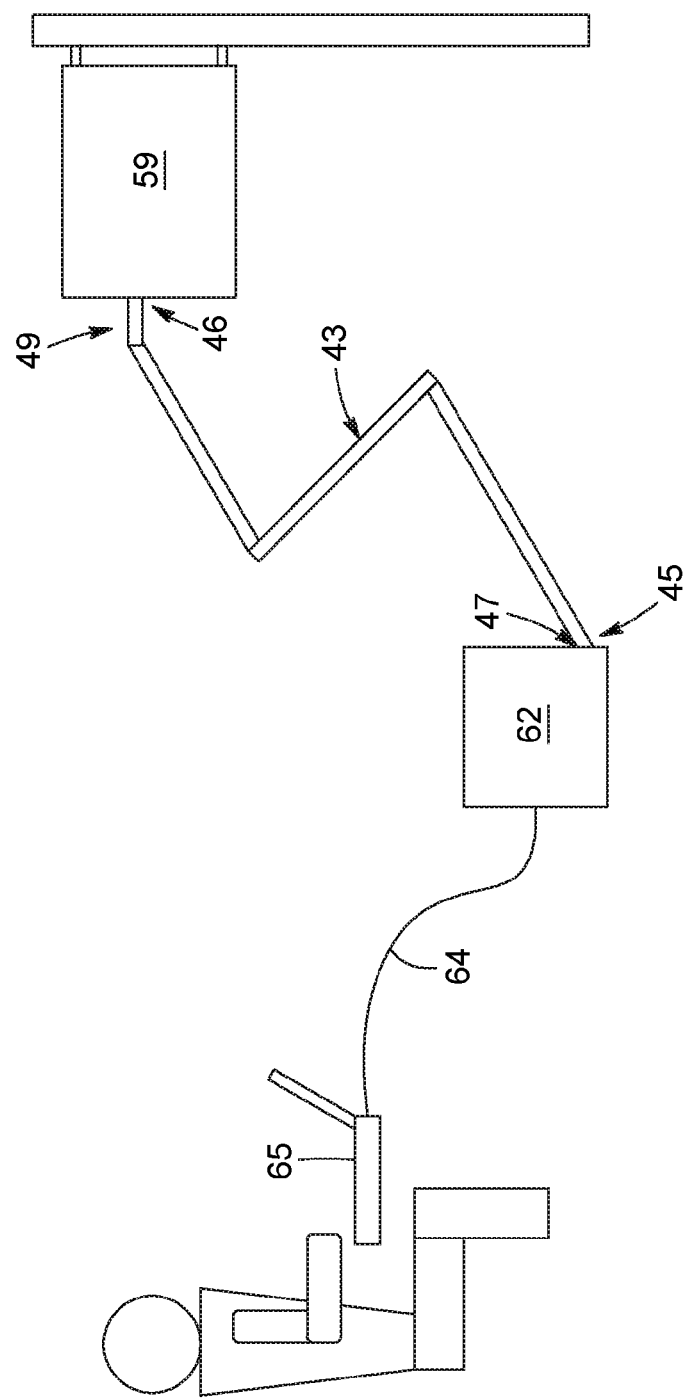
FIG. 3 illustrates an optical system for imaging a surface covered with a viscous substance and comprising an articulated arm according to one embodiment.

In some embodiments, and now referring to FIG. 3., the optical system 1 may include an instrument rack 62 and an instrument head 59 to be used for inspecting hard-to-reach and/or large areas. More particularly, this configuration could be used for performing inspections of surfaces in a more automated manner. The instrument head 59 contains the light source 23, the camera 25 and related optical elements, and the flattening plate 19.

In some embodiments, the optical system 1 may also include an articulated arm 43. The articulated arm has a proximal extremity 45, configured to be affixed to an anchoring point 47, and a distal extremity 46, which comprises a frame-mounting structure 49 configured for connection with the support frame 9. The articulated arm may be particularly useful when imaging hard-to-reach areas. The instrument head 59 is attached to the articulated arm 43 to accurately place the instrument head 59 over the surface 3 to be inspected.

Optionally, the articulated arm 43 is powered by electrical motors, and/or by hydraulic or pneumatic pistons. The power supply and control electronics of the instrument head 59 and the power supply and control electronics of the articulated arm 43 are housed in a common instrument rack 62. The instrument rack 62 and the instrument head 59 are typically placed inside the object (e.g. a container) under inspection. The operator can remotely control the position of the articulated arm 43 and the operation of the light source 23 and the camera 25 by using, for example, a computer 65 operatively connected to the instrument rack 62 via electrical cabling 64.

In one embodiment, the light source 23 preferably provides a collimated illuminating beam 7 having a spectral profile including a terahertz imaging waveband to which the camera 25 is sensitive. The flattening plate 19 is preferably made from HDPE. The support frame 9 is preferably made from aluminum and has a length of approximately 100 cm and a cross-sectional surface area of 50×50 $cm^2$. The optical system 1 is configured to image an area of approximately 30×20 $cm^2$. Alternatively, the flattening plate 19, the light source 23, and the camera 25 can be configured to enable imaging of a surface through a substance that is transparent to a different imaging waveband (e.g. mm-wave, infrared, visible or ultraviolet).

The various embodiments of the optical system 1 of the present description may be particularly useful for addressing some of the challenges associated with actively imaging a metallic surface covered by a layer of an opaque and viscous substance. As previously described, the optical system 1 advantageously uses a light source 23 emitting an illuminating beam in a terahertz waveband, a terahertz camera 25 (sensitive to the spectral content of the illuminating beam) and a flattening plate 19 to produce clear and undistorted images of a surface 3 covered by the viscous substance, such as hydrocarbon-based substances.

In accordance with embodiments, there is also provided an optical method for imaging a surface through a viscous substance using an illuminating beam having a spectral profile including an imaging waveband to which the viscous substance is transparent.

The optical method comprises a step of flattening the viscous substance into a substantially flat layer with a flattening plate transparent to the imaging waveband, a step of projecting the illuminating beam towards the surface through the flattening plate, a step of detecting return light from at least a portion of the surface illuminated by the illuminating beam, and a step of processing said return light to obtain an image of said surface.

In some embodiments, the optical method further comprises a step of displaying said image of the surface.

In some embodiments, the optical method further comprises a step of providing a light source and a camera.

In some embodiments, the optical method further comprises a step of placing an optical system in contact with the surface.

In some embodiments, the optical method further comprises a step of directing the illuminating beam towards the inspected surface (that is in a plane parallel to a surface-abutting plane), and a step of directing the camera towards the inspected surface for collecting light reflected by the surface. In one variant, the step of directing the camera towards the inspected surface is carried out so as to collect specular light reflected by the surface.

In some embodiments, the return light corresponds to a specular reflection of the illuminating beam on the surface. In other variants, the detection of light diffused by the surface may also be envisioned.

Of course, numerous modifications could be made to the embodiments described above without departing from the scope of the appended claims.

The invention claimed is:

1. An optical system for imaging a surface covered with a viscous substance using an illuminating beam having a spectral profile including an imaging waveband to which the viscous substance is transparent, the optical system comprising:
   a support frame having a front end and a rear end, the support frame comprising an abutment structure defining a surface-abutting plane at said front end;
   a flattening plate transparent to the imaging waveband, the flattening plate extending across the support frame rearwardly of the surface-abutting plane and being engageable with the viscous substance to flatten the same into a substantially flat layer,
   a light source for generating the illuminating beam and operatively coupled to the support frame so as to project said illuminating beam towards the surface through the flattening plate; and
   a camera sensitive to light in said imaging waveband and mounted onto the support frame, the camera having a field of view encompassing at least a portion of the surface illuminated by the illuminating beam.

2. The optical system according to claim 1, further comprising a biasing assembly configured to bias the flattening plate towards the surface-abutting plane.

3. The optical system according to claim 2, wherein the biasing assembly comprises:
   a flange projecting inwardly of the support frame rearwardly of the flattening plate; and
   at least one spring connecting the flange to the flattening plate.

4. The optical system according to claim 1, wherein the flattening plate has two surfaces coated with an anti-reflection coating.

5. The optical system according to claim 1, wherein the abutment structure comprises a plurality of legs each having a forward extremity configured to engage the surface through the viscous substance.

6. The optical system according to claim 5, wherein each leg further comprises a surface-engaging wheel mounted at said forward extremity.

7. The optical system according to claim 1, further comprising an articulated arm having a proximal extremity configured to be affixed to an anchoring point and a distal extremity comprising a frame-mounting structure configured for connection with the support frame.

8. The optical system according to claim 1, wherein the light source and the camera are mounted proximate the rear end of the support frame.

9. The optical system according to claim 1, wherein the imaging waveband comprises a terahertz waveband extending from 0.15 to 0.6 terahertz.

10. The optical system according to claim 9, wherein the flattening plate is made of a polyethylene thermoplastic material.

11. The optical system according to claim 1, wherein the light source comprises at least one gigahertz sub-source and a frequency multiplier.

12. The optical system according to claim 1, wherein the camera is a terahertz-sensitive camera.

13. The optical system according to claim 1, further comprising a processor for processing images of the surface.

14. The optical system according to claim 1, further comprising a display for displaying the processed images of the surface.

15. An optical method for imaging a surface covered with a viscous substance using an illuminating beam having a spectral profile including an imaging waveband to which the viscous substance is transparent, the optical method comprising the steps of:
   flattening the viscous substance into a substantially flat layer with a flattening plate transparent to the imaging waveband;
   projecting the illuminating beam towards the surface through the flattening plate;
   detecting return light from at least a portion of the surface illuminated by the illuminating beam; and
   processing said return light to obtain an image of said surface.

16. The optical method according to claim 15, the method further comprising a step of displaying said image of the surface.

17. The optical method according to claim 15, wherein the return light corresponds to a specular reflection of the illuminating beam on the surface.

* * * * *